(12) United States Patent
Davis

(10) Patent No.: US 7,276,514 B2
(45) Date of Patent: Oct. 2, 2007

(54) PYRROLOQUINOLINE QUINONE DRUGS FOR TREATMENT OF CARDIAC INJURY AND METHODS OF USE THEREOF

(75) Inventor: Paul J. Davis, Albany, NY (US)

(73) Assignee: Charitable Leadership Foundation - Medical Technology Acceleration Program, Clifton Park, NY (US)

( * ) Notice: Subject to any disclaimer, the term of this patent is extended or adjusted under 35 U.S.C. 154(b) by 553 days.

(21) Appl. No.: 10/146,566

(22) Filed: May 15, 2002

(65) Prior Publication Data

US 2003/0216424 A1    Nov. 20, 2003

(51) Int. Cl.
*A01N 43/00* (2006.01)

(52) U.S. Cl. .................. 514/292; 514/359; 514/277; 514/183

(58) Field of Classification Search ............... 514/292
See application file for complete search history.

(56) References Cited

U.S. PATENT DOCUMENTS

| | | |
|---|---|---|
| 5,091,391 A | 2/1992 | Aizenman et al. |
| 5,145,862 A | 9/1992 | Aizenman et al. |
| 5,460,819 A | 10/1995 | Gallop et al. |
| 5,616,576 A | 4/1997 | Hauschka et al. |

FOREIGN PATENT DOCUMENTS

| | | |
|---|---|---|
| WO | WO93/10784 | 6/1993 |
| WO | WO94/01142 | 1/1994 |
| WO | WO98/43621 | 10/1998 |
| WO | WO 03/097056 A1 | 11/2003 |

OTHER PUBLICATIONS

Gallop, et al. (1989). TIBS 14: 343-346.
Hultquist, et al. (1993).Amer J Hemat 42: 13-18.
Jensen, et al. (1994). Neuroscience 62: 399-406.
Scanlon, et al. (1997). Euro J Pharm 326: 67-74.
Xu, et al. (1992). Proc Natl Acad Sci USA 89: 2130-2134.
Xu, et al. (1993). Biochem Biophys Res Commun 193: 434-439.
Zhang, et al. (1995). Biochem Biophys Res Commun 212: 41-47.
Hamagishi, et al., *J. Pharmacol. Experimental Therap.*, 255(3):980-985 (1990).
International Search Report for PCT/US03/15187, mailed Sep. 29, 2003.
Sugioka, et al., *Biochem. & Biophys. Acta*, 964(2):175-182 (1988).

*Primary Examiner*—Ardin H. Marschel
*Assistant Examiner*—Michel Graffeo
(74) *Attorney, Agent, or Firm*—Ivor R. Elrifi; Naomi S. Biswas; Mintz, Levin, Cohn, Ferris, Glovsky and Popeo, P.C.

(57) ABSTRACT

The invention includes composition comprising substantially purified pyrroloquinoline quinone, that are useful in methods for the treatment and prevention of cardiac injury caused by hypoxia or ischemia. The invention also includes methods for the treatment and prevention of cardiac injury comprising contacting a compression of the invention with a human patient.

7 Claims, 9 Drawing Sheets

PYRROLOQUINOLINE QUINONE DRUGS FOR TREATMENT OF CARDIAC INJURY AND METHODS OF USE THEREOF

BACKGROUND OF THE INVENTION

The heart is critically dependent on uninterrupted blood flow for the delivery of oxygen and nutrients and the removal of harmful products of metabolism. Ischemia leads to rapid changes in myocardial metabolism and cellular injury, the extent of the injury being dependent upon the severity of ischemia. Continued ischemia leads to total tissue necrosis in a few hours.

Reperfusion, although generally considered beneficial, causes tissue injury by several mechanisms. Clinically, in open heart surgery, heart transplantation, and reversal of heart disease, protection of the myocardium against injury by ischemia-reperfusion is an issue of utmost clinical interest. Further, exacerbation of hypoxic injury after restoration of oxygenation (reoxygenation) by reperfusion is an important mechanism of cellular injury in other types of organ transplantation and in hepatic, intestinal, cerebral, renal, and other ischemic syndromes.

SUMMARY OF THE INVENTION

The present invention relates to the discovery that myocardial oxidative stress can be prevented or minimized by administration of certain cardioprotective factors, and thus has benefit for treating cardiovascular and other diseases. In particular, it has been found that non-toxic dosages of pyrroloquinoline quinone ("PQQ") drugs are useful as cardioprotective agents, and are therefore valuable in the treatment of a variety of various heart-related ailments such as ischemia-reperfusion injury, congestive heart failure, cardiac arrest and myocardial infarction such as due to coronary artery blockage, and for cardioprotection. PQQ in particular has been found to modulate myocardial oxidative stress such that myocardial cells (which are the subject of the oxidative stress) are protected from cell death.

The compositions and methods of the invention are surprisingly useful for the reduction or elimination of hypoxic/ischemic cardiac injury in vivo and ex vivo, as well as the prevention and/or treatment of cardiovascular disease in a mammals in need thereof, such as humans.

In another aspect of the invention, PQQ has been found to modulate, e.g., enhance or maintain the effect of, cardioprotective signaling pathways such as the regulation of the mitochondrial channel mitoK$_{ATP}$, the nitric oxide-protein kinase C pathway, and the angiotensin-converting enzyme pathway.

In another aspect of the invention, the present invention related to treating or preventing myocardial oxidative stress in myocardial cells in a subject by administering an agent that modulates myocardial oxidative stress such that the myocardial cells are protected from cell death.

In another aspect of the invention, the present invention related to treating or preventing myocardial hypoxic or ischemic damage in a subject by administering an agent that modulates myocardial hypoxic or ischemic damage such that myocardial cells are protected from cell death.

In another aspect of the invention, PQQ has been found to modulate free radical damage caused by myocardial oxidative stress. Free radicals generated by ischemic or hypoxic conditions have been found to be a significant cause of myocardial damage leading to myocardial death. As such, administration of PQQ, administered in vivo in non-toxic dosages, is an effective treatment for inhibiting or preventing myocardial oxidative stress free radical damage.

The invention further relates to methods of improving coronary blood flow in a subject by administering to the subject PQQ in a non-toxic amount, such that coronary blood flow is improved.

In one aspect, the present invention relates to treating or preventing cardiac injury caused by hypoxia or ischemia in a subject by administering pyrroloquinoline quinone, e.g., in an amount effective to treat or prevent cardiac injury. PQQ is typically administered at a non-toxic concentration, e.g., between about 1 nM and less than 10 µM, including less than 900 µM, less than 700 µM, less than 500 µM, less than 300 µM, less than 100 µM, or less than 50 µM. In other embodiments, PQQ may be administered at a concentration of about 1 to 10 µM. In other embodiments, PQQ is administered as a function of the subject's body weight. PQQ may typically be administered at a concentration of between about 1 µg/kg to 1 g/kg of a subject's body weight, including less than 500 mg/kg, 250 mg/kg, 100 mg/kg, 10 mg/kg, 5 mg/kg, 2 mg/kg, 1 mg/kg, 500 µg/kg, 250 µg/kg, 100 µg/kg, 10 µg/kg, 5 µg/kg, 2 µg/kg or 1 µg/kg.

The invention further includes cardioprotective agents containing PQQ, e.g, in an amount effective to effect cardioprotection, and a pharmaceutically acceptable carrier. Also included are kits for treating patients at risk of cardiac injury, stroke, or migraine headaches, containing in one or more containers, an effective amount of pyrroloquinoline quinone, a pharmaceutically acceptable carrier, and instructions for use.

In another aspect, the invention relates to treatment or prevention of cardiac injury caused by hypoxia or ischemia in vivo, by administration of an NADPH-dependent methemoglobin reductase substrate; and kits for use in treatment or prevention of cardiac injury, including an effective amount of an NADPH-dependent methemoglobin reductase substrate, a pharmaceutically acceptable carrier, and instructions for use. In some embodiments of the invention the NADPH-dependent methemoglobin reductase substrate is purified from erythrocytes, such as mammalian erythrocytes (e.g., human, bovine, or murine) or non-mammalian erythrocytes (e.g., *Rana catesbeiana*).

In yet another aspect, the invention relates to methods for preventing organ damage during organ or tissue transplantation, wherein PQQ is administered to an organ donor prior to and/or concurrent with removal of the organ or tissue; and kits for use in preventing organ damage during organ or tissue transplantation, including an effective amount of pyrroloquinoline quinone, a pharmaceutically acceptable carrier, and instructions for use.

In a further aspect, the invention relates to methods for preventing stroke, e.g., in subjects suffering from heart failure, by administering PQQ in amounts effective to obtain the desired protective effect. The PQQ may be desirably administered, e.g., at concentrations of about of about 1 to 10 µM.

The invention includes methods for treating heart failure in a subject by administering PQQ and one or more additional therapeutic compounds. In some embodiments, the additional therapeutic compound may be an anti-platelet drug, anti-coagulant drug and/or an anti-thrombotic drug, or combinations thereof.

In another aspect, the invention relates to methods of treating myocardial infarction in a subject by administering PQQ at levels such that the myocardial infarction is decreased or stabilized.

In yet another aspect, the invention relates to methods of preventing migraine headaches in a subject by treating the subject with PQQ The PQQ may be desirably administered, e.g., at concentrations of about of about 1 to 10 µM.

In yet another aspect, the invention relates to methods of preventing reperfusion injury in a subject suffering from or at risk of hypothermia, by treating the subject with PQQ. The PQQ may be desirably administered, e.g., at concentrations of about of about 1 to 10 µM.

The invention further relates to methods for preventing vascular occlusion following balloon angioplasty in a subject by pre-treating the subject with PQQ. The subject may be also pre-treated with PQQ and one or more additional therapeutic compounds (e.g., coumadin, angiotensin converting enzyme (ACE) inhibitors such as captopril, benazepril, enalapril, fosinopril, lisinopril, quinapril, ramipril, imidapril, peridopril erbumine and trandolapril, and ACE receptor blockers such as losartan, irbesartan, candesartan cilexetil and valsartan). In some embodiments, the additional therapeutic compound may be an anti-platelet drug, anti-coagulant drug and/or an anti-thrombotic drug, or combinations thereof In another aspect, the present invention involves a method for preventing or reducing reperfusion injury in a subject suffering from hypothermic injury by administering PQQ to the subject.

These and other objects of the present invention will be apparent from the detailed description of the invention provided below.

DETAILED DESCRIPTION OF THE INVENTION

Figure 1:
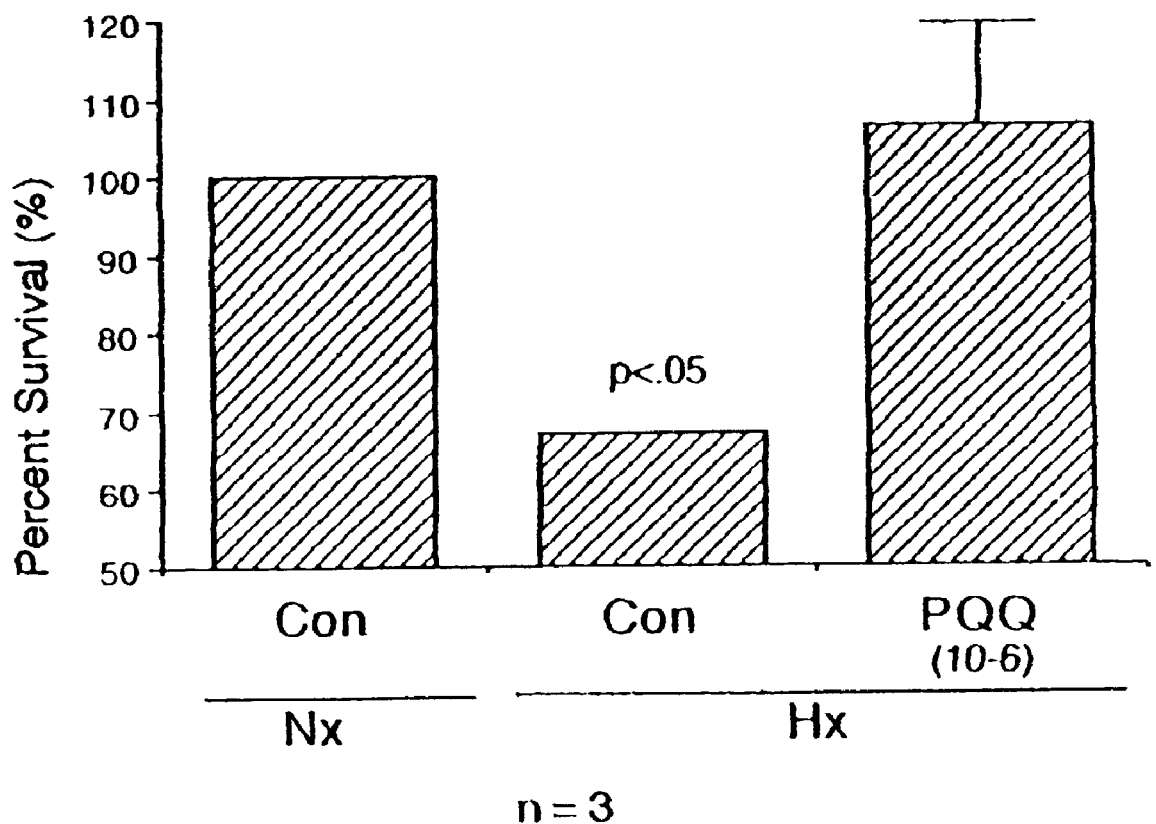
FIG. 1 is a bar graph demonstrating the increase in viable adult cardiac mouse myocytes following hypoxia by pre-treatment with PQQ.

The features and other details of the invention will now be more particularly described with reference to the accompanying drawings and pointed out in the claims. It will be understood that particular embodiments described herein are shown by way of illustration and not as limitations of the invention. The principal features of this invention can be employed in various embodiments without departing from the scope of the invention. All parts and percentages are by weight unless otherwise specified.

Definitions

For convenience, certain terms used in the specification, examples, and appended claims are collected here. Unless otherwise defined, all technical and scientific terms used herein have the same meaning as commonly understood by one of ordinary skill in the art to which this invention pertains. However, to the extent that these definitions vary from meanings circulating within the art, the definitions below are to control.

"Ischemia" includes the decrease or cessation of myocardial blood flow.

"Hypoxia" includes the deficiency in the amount of oxygen reaching body tissues.

"Hypoxia or ischemic-related injury" includes cardiac injury.

"Reperfusion" includes the restoration of blood flow to an organ or tissue that has had its blood supply cut off, as after a heart attack or stroke.

"Oxidative stress" includes conditions that occur when there is an excess of free radicals, a decrease in antioxidant levels, or both.

"Necrosis" includes the death of cells or tissues through injury or disease, particularly in a localized area of the body such as the myocardium.

"Apoptosis" refers to programmed cell death.

"Beta blockers" include agents such as atenolol, metoprolol, and propranolol, which act as competitive antagonists at the adrenergic beta receptors. Such agents also include those more selective for the cardiac (beta-1) receptors which allows for decreased systemic side effects. Beta blockers reduce the symptoms connected with hypertension, cardiac arrhythmias, migraine headaches, and other disorders related to the sympathetic nervous system. Beta blockers also are sometimes given after heart attacks to stabilize the heartbeat. Within the sympathetic nervous system, beta-adrenergic receptors are located mainly in the heart, lungs, kidneys, and blood vessels. Beta blockers compete with the nerve-stimulating hormone epinephrine for these receptor sites and thus interfere with the action of epinephrine, lowering blood pressure and heart rate, stopping arrhythmias, and preventing migraine headaches.

"Cardiac injury" includes any chronic or acute pathological event involving the heart and/or associated tissue (e.g., the pericardium, aorta and other associated blood vessels), including ischemia-reperfusion injury; congestive heart failure; cardiac arrest; myocardial infarction; cardiotoxicity caused by compounds such as drugs (e.g., doxorubicin, herceptin, thioridazine and cisapride); cardiac damage due to parasitic infection (bacteria, fungi, rickettsiae, and viruses, e.g., syphilis, chronic *Trypanosoma cruzi* infection); fulminant cardiac amyloidosis; heart surgery; heart transplantation; and traumatic cardiac injury (e.g penetrating or blunt cardiac injury, aortic valve rupture).

"Subject" includes living organisms such as humans, monkeys, cows, sheep, horses, pigs, cattle, goats, dogs, cats, mice, rats, cultured cells therefrom, and transgenic species thereof. In a preferred embodiment, the subject is a human. Administration of the compositions of the present invention to a subject to be treated can be carried out using known procedures, at dosages and for periods of time effective to treat the condition in the subject. An effective amount of the therapeutic compound necessary to achieve a therapeutic effect may vary according to factors such as the age, sex, and weight of the subject, and the ability of the therapeutic compound to treat the foreign agents in the subject. Dosage regimens can be adjusted to provide the optimum therapeutic response. For example, several divided doses may be administered daily or the dose may be proportionally reduced as indicated by the exigencies of the therapeutic situation.

"Substantially pure" includes compounds, e.g., drugs, proteins or polypeptides that have been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state. Included within the meaning of the term "substantially pure" are compounds, such as proteins or polypeptides, which are homogeneously pure, for example, where at least 95% of the total protein (by volume, by wet or dry weight, or by mole percent or mole fraction) in a sample is the protein or polypeptide of interest.

"Administering" includes routes of administration which allow the compositions of the invention to perform their intended function, e.g, treating or preventing cardiac injury caused by hypoxia or ischemia. A variety of routes of administration are possible including, but not necessarily limited to parenteral (e.g., intravenous, intraarterial, intramuscular, subcutaneous injection), oral (e.g., dietary), topical, nasal, rectal, or via slow releasing microcarriers depending on the disease or condition to be treated. Oral, parenteral and intravenous administration are preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils Intravenous vehicles can include various additives, preservatives, or fluid, nutrient or electrolyte replenishers (See generally, *Remington's Pharmaceutical Science*, 16th Edition, Mack, Ed. (1980)).

"Effective amount" includes those amounts of pyrroloquinoline quinone which allow it to perform its intended function, e.g., treating or preventing, partially or totally, cardiac injury caused by hypoxia or ischemia as described herein The effective amount will depend upon a number of factors, including biological activity, age, body weight, sex, general health, severity of the condition to be treated, as well as appropriate pharmacokinetic properties. For example, dosages of the active substance may be from about 0.01 mg/kg/day to about 500 mg/kg/day, advantageously from about 0.1 mg/kg/day to about 100 mg/kg/day. A therapeutically effective amount of the active substance can be administered by an appropriate route in a single dose or multiple doses. Further, the dosages of the active substance can be proportionally increased or decreased as indicated by the exigencies of the therapeutic or prophylactic situation.

"Specific binding" or "specifically binds" includes proteins, such as an antibody which recognizes and binds an pyrroloquinoline quinone or a ligand thereof, but does not substantially recognize or bind other molecules in a sample.

"Pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

"Pharmaceutically acceptable esters" includes relatively non-toxic, esterified products of therapeutic compounds of the invention. These esters can be prepared in situ during the final isolation and purification of the therapeutic compounds or by separately reacting the purified therapeutic compound in its free acid form or hydroxyl with a suitable esterifying agent; either of which are methods known to those skilled in the art. Acids can be converted into esters according to methods well known to one of ordinary skill in the art, e.g., via treatment with an alcohol in the presence of a catalyst.

"Additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, e.g., in *Remington's Pharmaceutical Sciences*.

"Unit dose" includes a discrete amount of the pharmaceutical composition comprising a predetermined amount of the active ingredient.

Pyrroloquinoline quinone (PQQ) is a water soluble anionic quinone that can transfer electrons catalytically between a variety of reductants and oxidants, and may be part of a soluble electron transport system in eukaryotic cells. PQQ proper is of the general structure

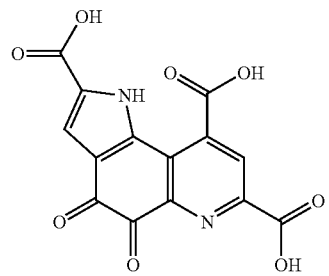

"Pyrroloquinoline quinone" includes any member of the pyrroloquinoline quinone family having chemical similarity, including closely related isomeric and stereoisomeric analogs of PQQ (See e.g., Zhang et al., 1995, *Biochem. Biophys. Res. Commun.* 212: 41-47, 1995). PQQ is also known as methoxatin. PQQ is found in animal tissues and fluids. Without wishing to be bound by theory, PQQ may act in part as a free-radical scavenger, particularly of reactive oxygen species (ROS). As such, PQQ may function as an NADPH-dependent methemogloblin reductase substrate (See e.g.: Xu et al., *Proc. Natl. Acad. Sci. USA,* 1992, 89(6):2130-4). Other NADPH-dependent methemogloblin reductase substrates may function to decrease or eliminate hypoxia or ischemia-related cardiac injury.

Compositions comprising substantially purified pyrroloquinoline quinone may include pyrroloquinoline quinone alone, or in combination with other components such as beta blockers, and compounds which are effective to favorably modulate cardioprotective signaling pathways such as phenylephrine, sphingosine-1-phosphate, or the ganglioside GM-1. Pyrroloquinoline quinone may be substantially purified by any of the methods well known to those skilled in the art. (ee, e.g., E. J. Corey and Alfonso Tramontano, J. Am. Chem. Soc., 103, 5599-5600 (1981); J. A. Duine, Review *Ann. Rev. Biochem.* 58, 403 (1989)).

The pyrroloquinoline quinone of the invention is, in one embodiment, a component of a pharmaceutical composition, which may also comprise buffers, salts, other proteins, and other ingredients acceptable as a pharmaceutical composition. The invention also includes a modified form of pyrroloquinoline quinone, which is capable of preventing or reducing hypoxic/ischemic cardiac injury as described herein.

The structure of the therapeutic compounds of this invention may include asymmetric carbon atoms. It is to be understood accordingly that the isomers (e.g., enantiomers and diastereomers) arising from such asymmetry are included within the scope of this invention. Such isomers can be obtained in substantially pure form by classical separation techniques and by sterically controlled synthesis. For the purposes of this application, unless expressly noted to the contrary, a therapeutic compound shall be construed to include both the R or S stereoisomers at each chiral center. In certain embodiments, an therapeutic compound of the invention comprises a cation. If the cationic group is hydrogen, $H^+$, then the therapeutic compound is considered an acid. If hydrogen is replaced by a metal ion or its equivalent, the therapeutic compound is a salt of the acid. Pharmaceutically acceptable salts of the therapeutic compound are within the scope of the invention, e.g., pharmaceutically acceptable alkali metal (e.g., $Li^+$, $Na^+$, or $K^+$) salts, ammonium cation salts, alkaline earth cation salts (e.g., $Ca^{2+}$, $Ba^{2+}$, $Mg^{2+}$), higher valency cation salts, or polycationic counter ion salts (e.g., a polyammonium cation). (See, e.g., Berge et al. (1977) "Pharmaceutical Salts", *J. Pharm. Sci.* 66:1-19). It will be appreciated that the stoichiometry of an anionic compound to a salt-forming counter ion (if any) will vary depending on the charge of the anionic portion of the compound (if any) and the charge of the counter ion. Preferred pharmaceutically acceptable salts include a sodium, potassium or calcium salt, but other salts are also contemplated within their pharmaceutically acceptable range.

The invention relates to methods of treating or preventing myocardial oxidative stress, such as is caused by hypoxia or ischemia, in a subject. This is done by administering to a subject in need thereof a preferably non-toxic amount of an agent such as PQQ which modulates myocardial oxidative stress such that the myocardial cells which are the target of the oxidative stress are protected from cell death. The cell death may be due, e.g., to necrosis or apoptosis.

Cardioprotective signaling pathways are known in the art. These pathways may be targeted for enhancement in patients in need of cardioprotection, by administering, pyrroloquinoline quinone in an amount effective to enhance or maintain the effect of cardioprotective signaling pathway.

Free radicals generated by ischemic or hypoxic conditions have been found to be a significant cause of myocardial damage leading to myocardial death. As such, administration of PQQ, administered in vivo, e.g., in non-toxic dosages, is an effective treatment for inhibiting or preventing myocardial oxidative stress free radical damage, either by PQQ-mediated free radical scavenging, or by inhibition of free radical generation.

Administration of the compounds of the invention may be done where clinically necessary or desirable, e.g., at the onset of reperfusion, or prior to reperfusion.

It has surprisingly also been found that coronary flow may be beneficially improved in a subject, e.g., one suffering from a low blood flow condition, by administering to a subject in need thereof a non-toxic amount of pyrroloquinoline quinone. This is illustrated in the Examples. Coronary flow may be measured by several indicators, such as the left ventricular diastolic pressure ("LVDP") or the left ventricular ("LVEDP"). Measurement of coronary flow, such as by determining LVDP or LVEDP, is within the skill of those in the art.

Cardiac injury caused by hypoxia or ischemia, such as myocardial infarction, may therefore be treated or prevented by administration of pyrroloquinoline quinone, preferably in a non-toxic dosage, e.g., at a concentration of less than about 10 µM.

The invention encompasses methods of treating or preventing cardiac injury caused by hypoxia or ischemia in a subject, wherein PQQ is administered to a subject in need thereof, such that hypoxia or ischemic-related injury is prevented or decreased. In certain embodiments, the PQQ is administered at a concentration of less than about 10 µM. In other embodiments, the PQQ is administered at a concentration in the range of about 10 nM to about 10 µM, about 10 nM to about 1 µM, 100 nM to about 10 µM, and 100 nM to about 500 nM. In still other embodiments of the invention, the PQQ is administered at a concentration such that the concentration of PQQ at the site of cardiac tissue is in the range of 10 nM to about 10 µM. PQQ may also be administered as a function of the subject's body weight. In some embodiments of the invention, PQQ is administered at a concentration of between about 1 µg/kg to 1 g/kg of a subject's body weight, including less than 500 mg/kg, 250 mg/kg, 100 mg/kg, 10 mg/kg, 5 mg/kg, 2 mg/kg, 1 mg/kg, 500 µg/kg, 250 µg/kg, 100 µg/kg, 10 µg/kg, 5 µg/kg, 2 µg/kg or 1 µg/kg. In further embodiments of the invention, the PQQ is administered at a non-toxic concentration, which includes concentrations of PQQ which are cytostatic but not cytotoxic, and concentrations which are cytotoxic to cell types other than the intended one or more cell types (e.g., cardiomyocytes). The determination of the cytotoxicity of a known concentration of PQQ to one or more cell types is within the abilities of one of ordinary skill in the art. By way of non-limiting example, toxicity to cultured adult mouse cardiac myocytes is observed at a concentration of 100 µM PQQ. In some embodiments, PQQ is administered in combination with other compounds, such as anti-platelet drugs, anti-coagulant drugs, and anti-thrombotic drugs.

The cardiac injury that can be treated or prevented by the methods and compositions of the present invention includes all cardiac injury caused or affected by hypoxia and/or ischemia. Such injury includes, but is not limited to, ischemia-reperfusion injury, congestive heart failure, myocardial infarction, cardiotoxicity caused by compounds such as drugs (e.g., doxorubicin), cardiac damage due to parasitic infection, fulminant cardiac amyloidosis, heart surgery, heart transplantation, and traumatic cardiac injury. All or a portion of the heart may be injured, including associated blood vessels and/or tissue, such as the pericardium.

The invention also encompasses a method of treating or preventing cardiac injury caused by hypoxia or ischemia in a subject, by administering to a subject in need thereof an NADPH-dependent methemoglobin reductase substrate, such that said hypoxia or ischemic-related injury is prevented or decreased. In embodiments of the invention, the NADPH-dependent methemoglobin reductase substrate is purified from erythrocytes, such as mammalian erythrocytes (e.g., human, bovine, or murine) or non-mammalian erythrocytes (e.g., *Rana catesbeiana*). One of ordinary skill in the art will know how to isolate and purify NADPH-dependent methemoglobin reductase substrates with minimal experimentation.

The invention further encompasses a method of preventing organ or tissue damage during organ or tissue transplantation, by administering to a donor pyrroloquinoline quinone prior to or concurrent with removal of said organ or tissue, such that damage caused by reperfusion of said organ or tissue is decreased or prevented. In preferred embodiments, the organ or tissue to be transplanted is the heart or cardiac tissue. The PQQ may also be contacted with the organ or tissue following surgical removal of the organ or tissue from the donor. In some embodiments, the PQQ is added in addition to known organ or tissue preservation solutions, such as University of Wisconsin solution or Celsior solution (See, e.g Thabut et al., *Am J Respir Crit Care Med*, 2001, 164(7):1204-8; Faenza et al., *Transplantation*, 2001,72(7): 1274-7).

The invention still further encompasses methods of preventing stroke in a subject (e.g., a human) suffering from heart failure, by treating a subject with pyrroloquinoline quinone and a pharmaceutically acceptable carrier. In some embodiments, the pyrroloquinoline quinone is administered to the subject at a concentration of less than about 10 µM. The PQQ may be administered prior to, or concomitant with, a surgical procedure that may increase the likelihood of a stroke in the patient. In one embodiment, the procedure is balloon angioplasty. Other procedures include coronary artery bypass surgery and valve replacement surgery. The PQQ may be administered prior to, concomitant with, or after anti-thrombogenic agents (e.g., coumadin).

The invention also encompasses methods of reducing or preventing headaches in a subject (such as a human), by treating the subject with pyrroloquinoline quinone and a pharmaceutically acceptable carrier. Such headaches include acute and chronic migraine headaches and sinus headaches.

The invention still further encompasses a method of preventing reperfusion injury in a subject (such as a human) suffering from hypothermia, by treating the subject with pyrroloquinoline quinone and a pharmaceutically acceptable carrier. The subject may be treated with PQQ prior to or concomitant with the standard rewarming procedures for treating a person suffering from hypothermia as are generally known in the art.

The invention encompasses the preparation and use of pharmaceutical compositions comprising a compound useful for the prevention or reduction of hypoxic/ischemic cardiac injury as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a pharmaceutically acceptable ester or salt, such as in combination with a physiologically-acceptable cation or anion, as is well known in the art. Further, the pyrroloquinoline quinone may contain pharmacologically acceptable additives (e g carrier, excipient and diluent), stabilizers or components necessary for formulating preparations, which are generally used for pharmaceutical products, as long as it does not adversely affect the efficacy of the preparation, e.g., in decreasing or inhibiting ischemia or reperfusion injury.

Examples of additives and stabilizers include saccharides such as monosaccharides (e.g., glucose and fructose), disaccharides (e.g., sucrose, lactose and maltose) and sugar alcohols (e.g., mannitol and sorbitol); organic acids such as citric acid, maleic acid and tartaric acid and salts thereof (e.g., sodium salt, potassium salt and calcium salt); amino acids such as glycine, aspartic acid and glutamic acid and salts thereof (e.g., sodium, calcium or potassium salt); surfactants such as polyethylene glycol, polyoxyethylene-polyoxypropylene copolymer and polyoxyethylenesorbitan fatty acid ester; heparin; and albumin.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. The preferred mode is intravenous administration.

The pyrroloquinoline quinone and the above-mentioned ingredients are admixed as appropriate to give powder, granule, tablet, capsule, syrup, injection and the like. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. The amount of the active ingredient is generally equal to the dosage of the active ingredient, which would be administered to a subject, or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Particularly contemplated additional agents include antiemetics and scavengers such as cyanide and cyanate scavengers. Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include potato starch and sodium starch glycollate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in, e.g., U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, a gel or cream or solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

Additional delivery methods for administration of compounds include a drug delivery device, such as that described in U.S. Pat. No. 5,928,195.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or diglycerides. Other parentally-administrable formulations that are useful include those, which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w)

active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e., by rapid inhalation through the nasal passage from a container of the powder held close to the nose.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations that are useful include those, which comprise the active ingredient in microcrystalline form or in a liposomal preparation.

The mixture of pyrroloquinoline quinone and pharmacologically acceptable additives is preferably prepared as a lyophilized product, and dissolved when in use. Such preparation can be prepared into a solution containing about 0.01-100.0 mg/ml of pyrroloquinoline quinone, by dissolving same in distilled water for injection or sterile purified water. More preferably, it is adjusted to have a physiologically isotonic salt concentration and a physiologically desirable pH value (pH 6-8).

While the dose is appropriately determined depending on symptom, body weight, sex, animal species and the like, it is generally assumed that treatment options holding the blood concentration at about 1 µM will be preferred. This plasma concentration may be achieved through administration of one to several doses a day. When pyrroloquinoline quinone is to be administered to a subject, 0.1 ng to 10 mg/kg body weight (e.g., 1 ng to 1 mg/kg body weight) of pyrroloquinoline quinone can be given intravenously.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXAMPLES

These Examples are provided for the purpose of illustration only and the invention should in no way be construed as being limited to these Examples, but rather should be construed to encompass any and all variations which become evident as a result of the teaching provided herein.

Example 1

In vitro Studies of PQQ Preservation of Cardiac Myocyte Viability

Figure 2:
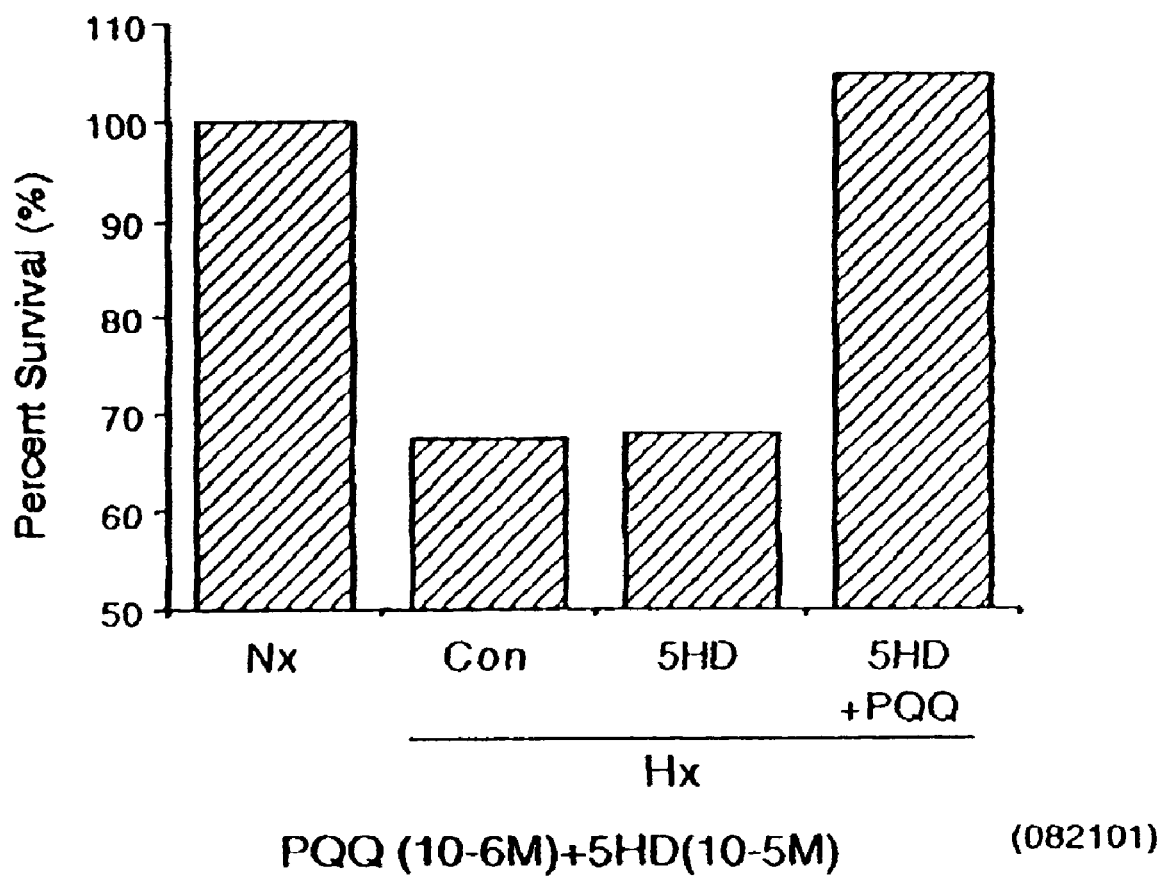
FIG. 2 is a bar graph showing that PQQ protection is not inhibited by 10 µM 5-hydroxydecanoic acid, a mitochondrial $K_{ATP}$ channel inhibitor.

An in vitro model of cultured adult cardiac mouse myocytes was developed to study cardioprotection by PQQ. These cells are viable in culture for up to 48 hours at a physiologic pH and consist of >90% rod-shaped cells. These cells can be used readily for determination of cell viability by trypan blue exclusion, and for biochemical, immunochemical, and molecular studies. In this model, approximately 35% of the cells die when exposed to 0% oxygen in a hypoxia chamber for 2-3 hours. As shown in FIG. 1, 1 µM PQQ added 1 hour before subjecting the cells to severe hypoxia (0% oxygen for 2-3 hours) produces a significant increase in the proportion of viable cells as indicated by trypan blue exclusion. A higher concentration of PQQ (100 µM) is highly toxic under normoxic conditions as evidenced by 100% cell death. FIG. 2 demonstrates that 1 µM PQQ protection against hypoxia-induced cell death is not inhibited by 100 µM 5-hydroxydecanoic acid, a mitrochondrial $K_{ATP}$ channel inhibitor. Without wishing to be bound by theory, these data suggest that PQQ does not exert cardioprotection by opening mitochondrial $K_{ATP}$ channels.

Example 2

Ex vivo Studies of PQQ Preservation of Cardiac Function

Ex vivo studies were performed using an isolated mouse heart preparation employing the Langendorff technique. In this approach, the heart is removed and mounted on a perfusion apparatus in which drugs can be given via an aortic cannula. The heart is paced at a constant rate, and left ventricular developed pressure [LVDP; left ventricular systolic pressure minus left ventricular end-diastolic pressure], left ventricular end-diastolic pressure [LVEDP], and the maximum positive and negative first derivatives of left ventricular pressure [+dP/dtmax and −dP/dtmax] are recorded. The heart is equilibrated for 20 min. After drug or vehicle is infused, the heart is subjected to 20 min of ischemia [coronary flow completely stopped] followed by 30 min of reperfusion. Coronary sinus flow as a reflection of coronary blood flow is also measured. This protocol leads to severe myocardial injury as measured by hemodynamic parameters.

Figure 3:
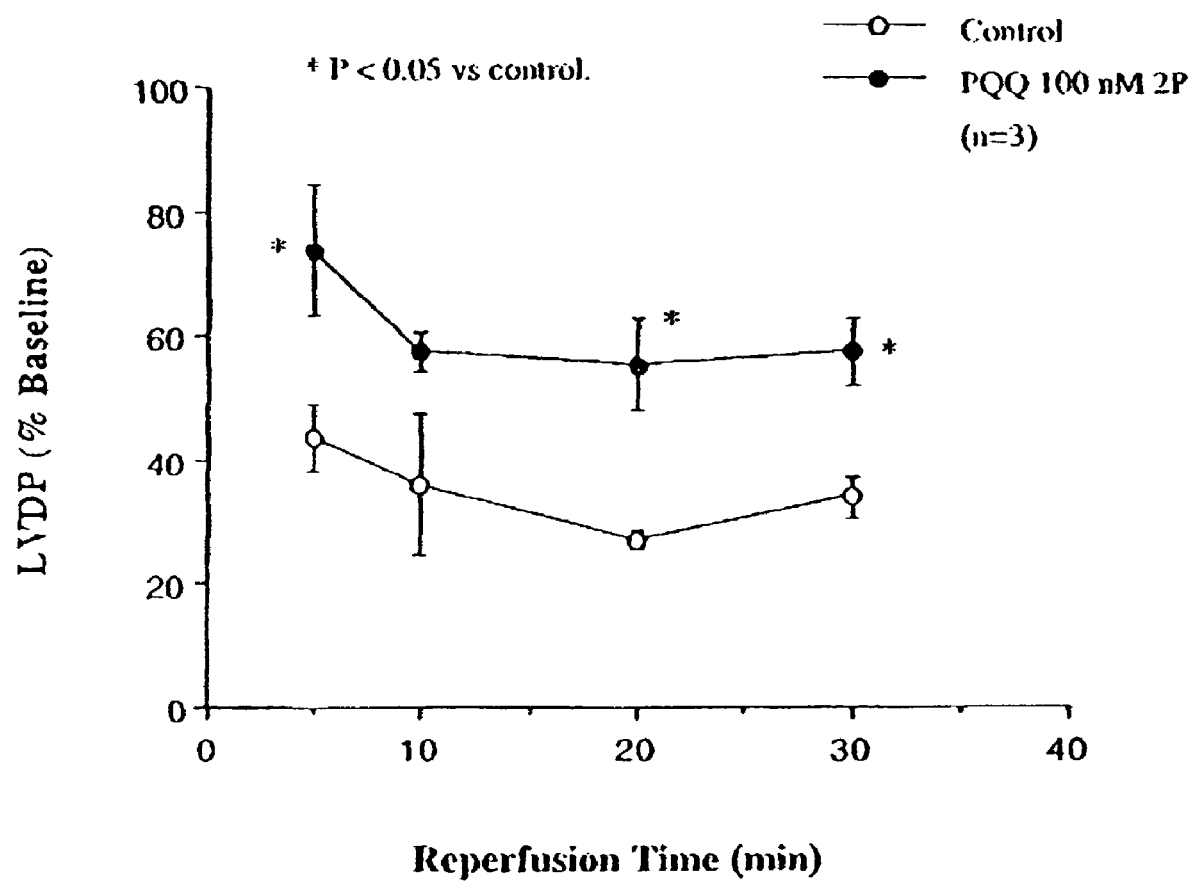
FIG. 3 is a line graph demonstrating that PQQ treatment prior to ischemia preserves left ventricular developed pressure (LVDP).
Figure 4:
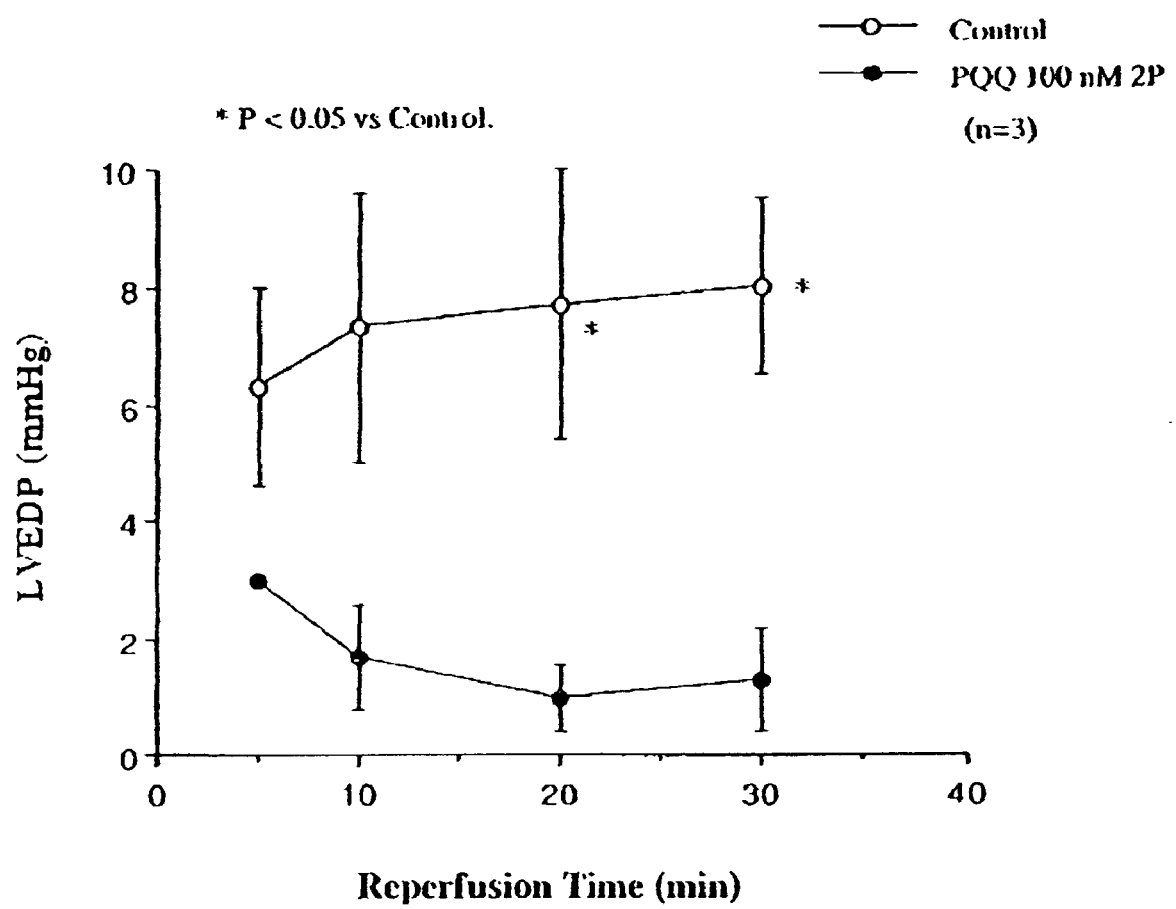
FIG. 4 is a line graph demonstrating that PQQ treatment prior to ischemia preserves left ventricular end-diastolic pressure (LVEDP; left ventricular systolic pressure minus left ventricular end-diastolic pressure).
Figure 5:
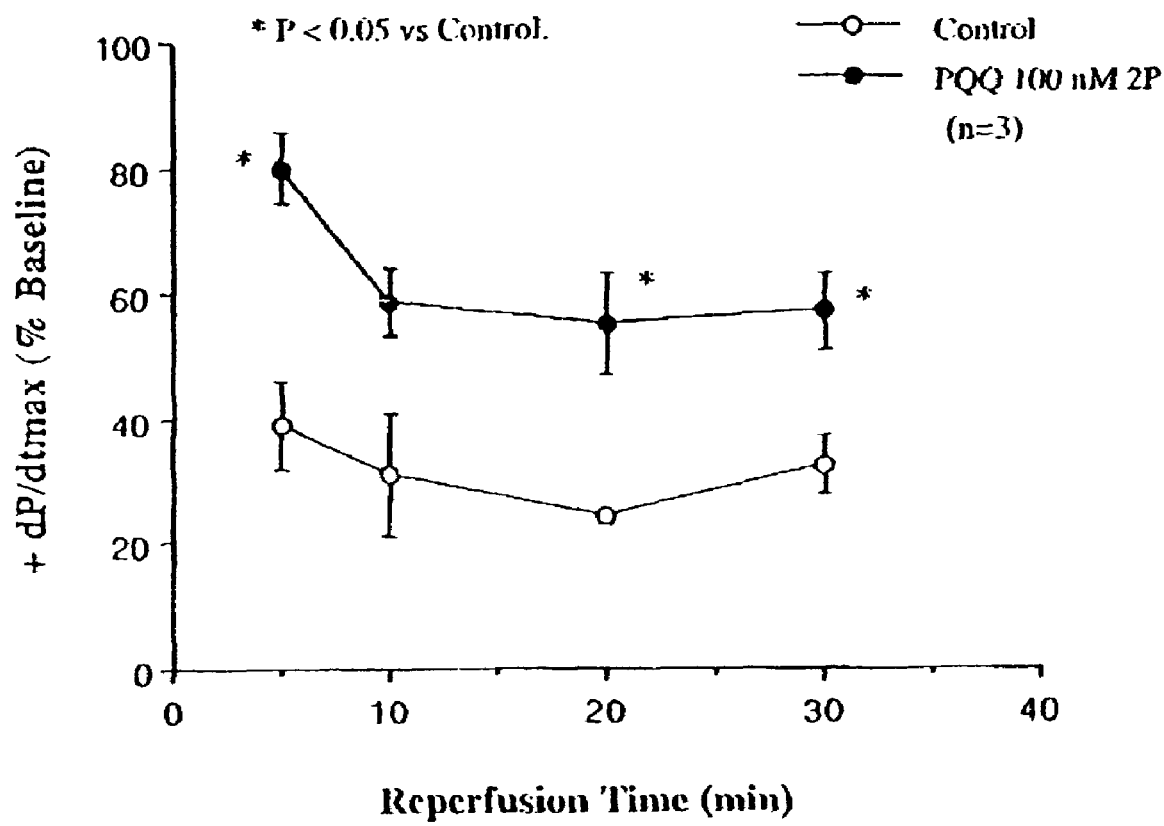
FIG. 5 is a line graph demonstrating the effect of PQQ treatment prior to ischemia as measured by the maximum positive first derivative of left ventricular pressure (LVDP).
Figure 6:
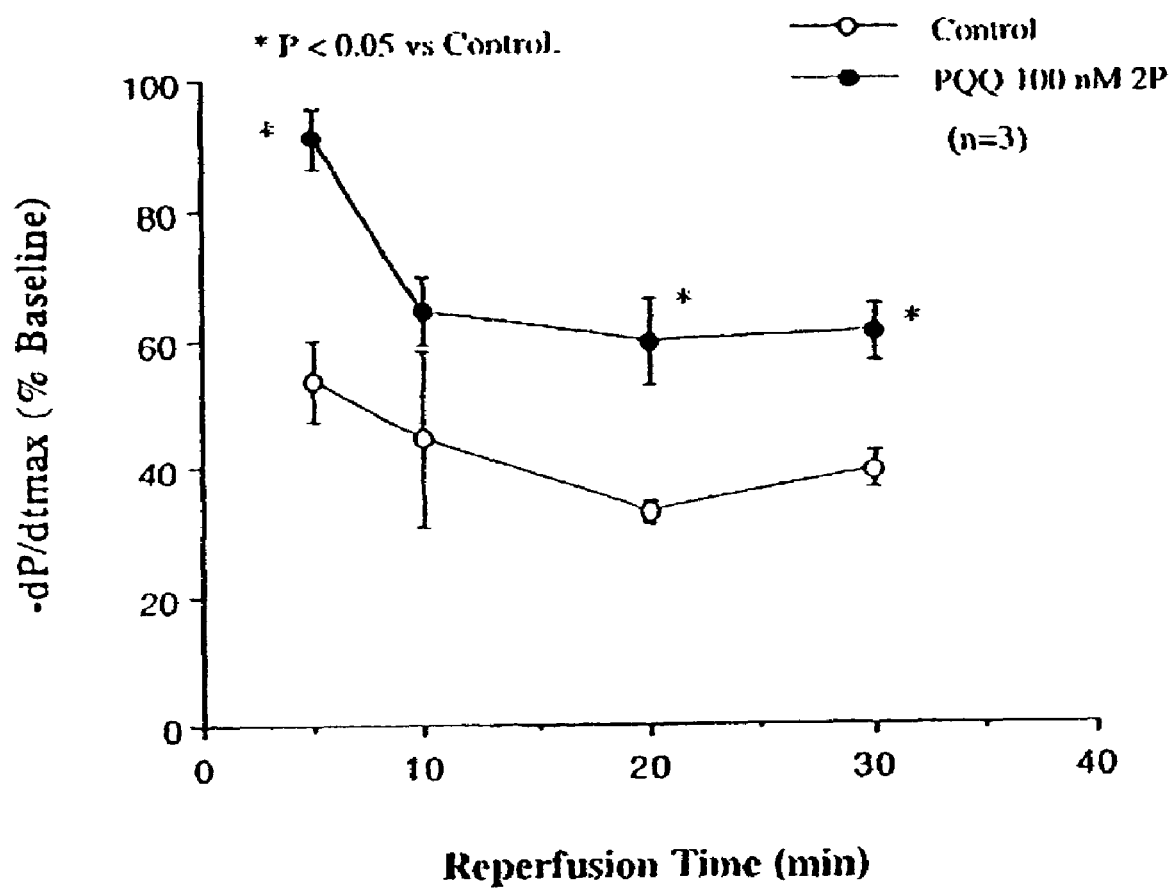
FIG. 6 is a line graph demonstrating the effect of PQQ treatment prior to ischemia as measured by the maximum negative first derivative of left ventricular pressure (LVDP).
Figure 7:
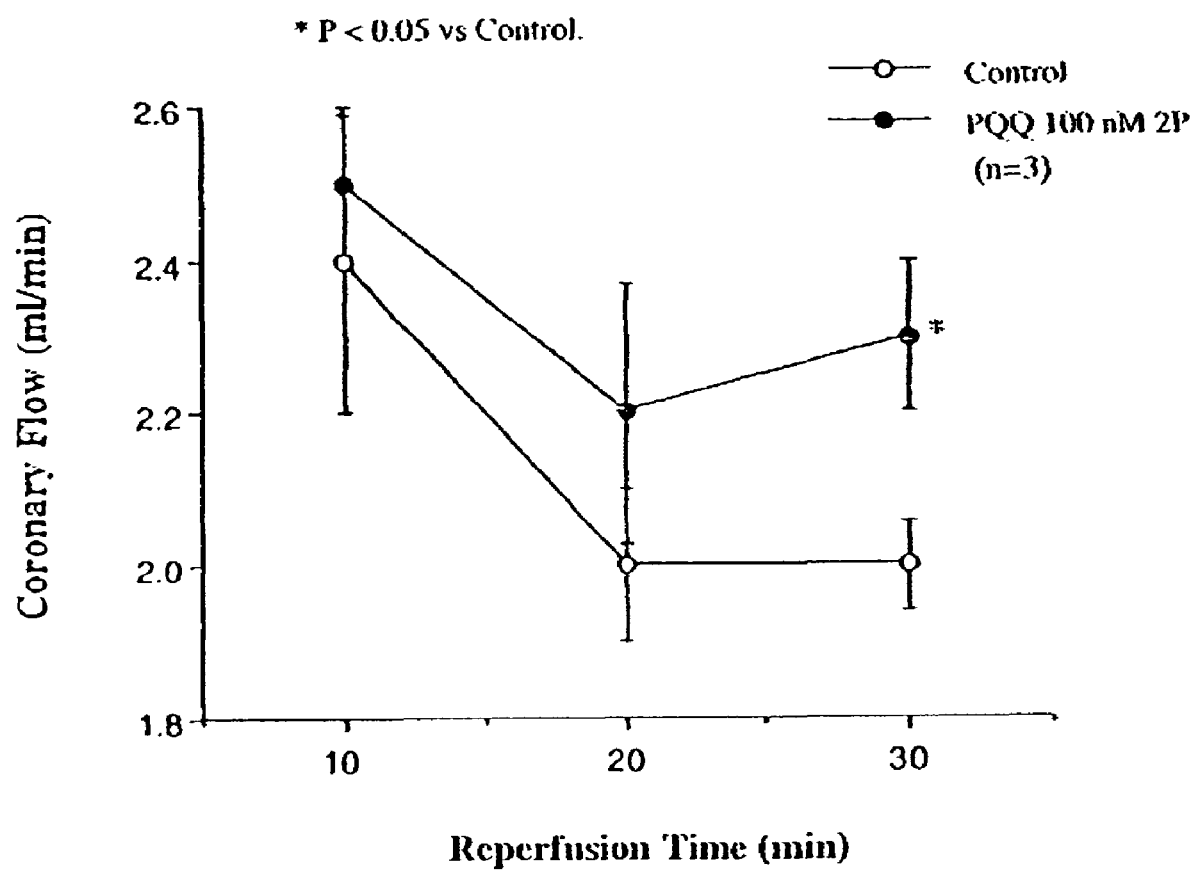
FIG. 7 is a line graph showing that coronary blood flow is significantly improved by PQQ treatment as compared to control.

As seen in FIG. 3, 100 nM PQQ infused for only 2 minutes prior to complete cessation of coronary blood flow produces significant preservation of LVDP Baseline 1. VDP averages 60 mmHg. Similar results are obtained with LVEDP [FIG. 4] Baseline LVEDP averages 8 mm Hg. (Note that an increase in LVEDP represents an adverse response). As expected, the data for + and −dP/dtmax track the LVDP results [FIGS. 5 and 6]. Similarly, coronary flow is significantly improved by PQQ pretreatment compared to control [FIG. 7].

Figure 8:
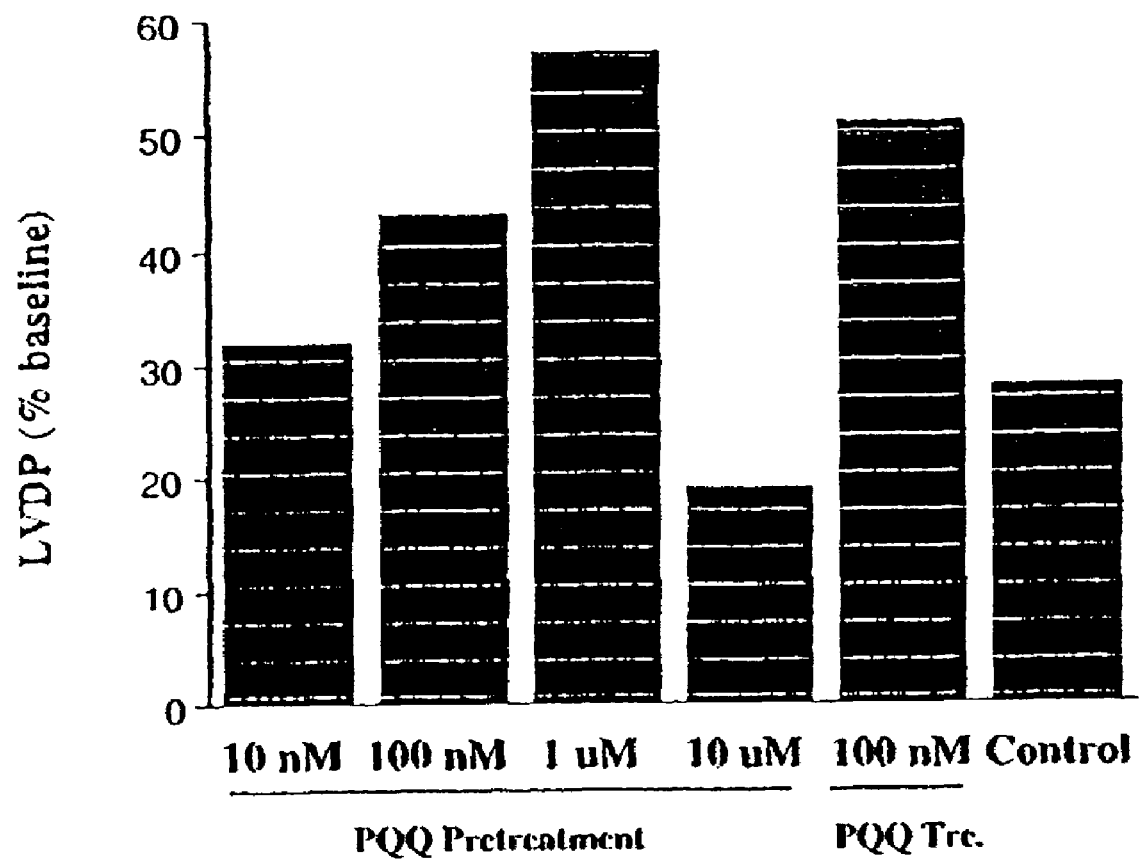
FIG. 8 is a bar graph indicating that 2 minutes of pretreatment with PQQ at several concentrations shown has progressively favorable responses between 10 nM and 1 µM, but that toxicity occurs at 10 µM.

In FIG. 8, it is shown that 2 min of pretreatment with PQQ at the concentrations shown has progressively favorable responses between 10 nM and 1 µM, but that toxicity occurs at 10 µM. Of major interest is that 100 nM PQQ given at the time of onset of reperfusion (PQQ tre.) is equivalent to pretreatment. Therefore, PQQ is useful in both pretreatment, e.g., in cardiac or other surgical procedures, and after symptoms occur, e.g., in the acute critical cardiac events.

Figure 9:
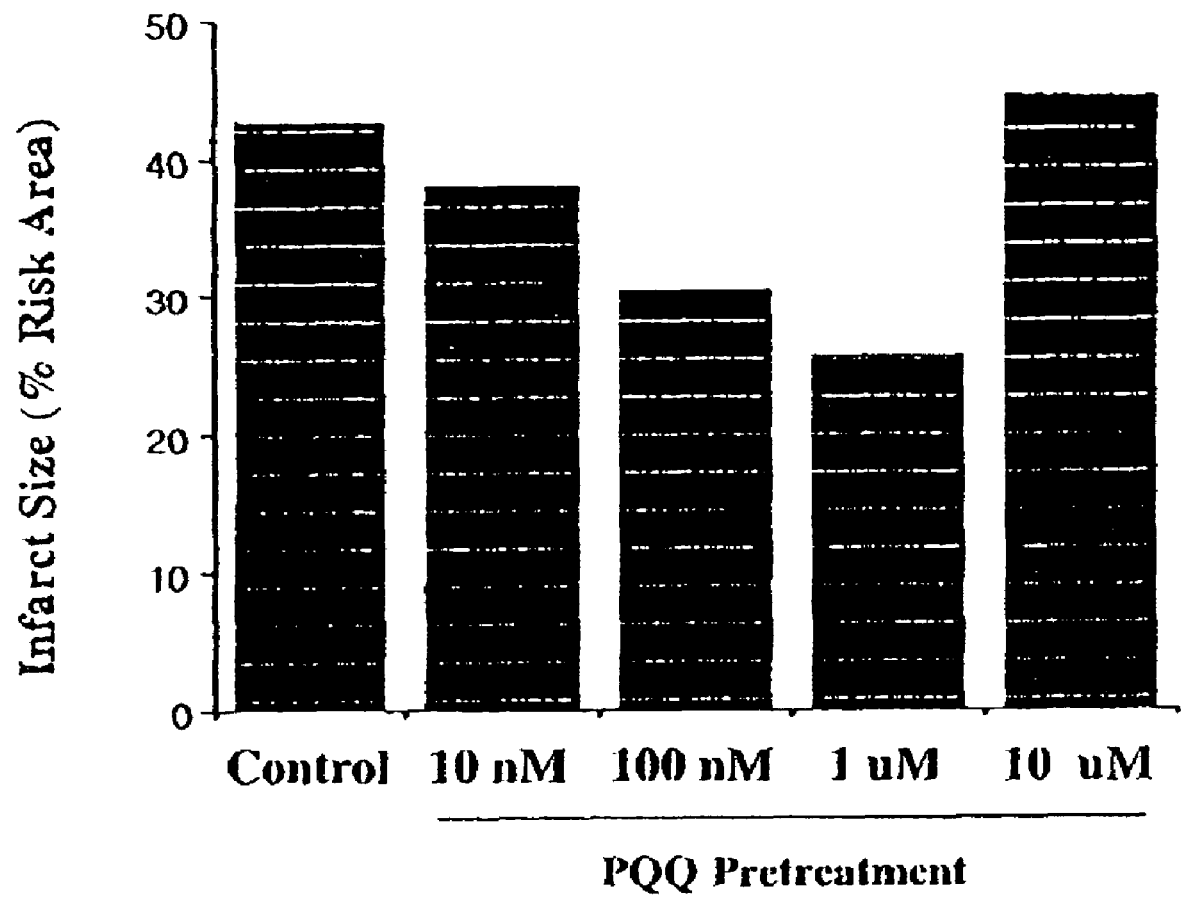
FIG. 9 is a bar graph demonstrating the changes in cardiac infarction size after PQQ pre-treatment. There is a progressive reduction in infarction size between 10 nM and 1 µM, but infarction size is not reduced at 10 µM PQQ.

FIG. 9 shows the results of experiments of infarct size measurements after PQQ pretreatment. As indicated, there is a progressive reduction in infarct size between 10 nM and 1 µM, paralleling the hemodynamic data. Consistent with the latter, infarct size is not reduced at 10 µM PQQ.

Example 3

PQQ Preservation of Oxidatively Stressed Cells

Cultured cardiac myocytes are subjected to oxidative stress by in vitro administration of $H_2O_2$. Two studies are done, one in which PQQ is added in concentrations between 10 nM and less than 10 µM to cardiac myocytes, after which $H_2O_2$ is added. In the other study, cardiac myocytes are subjected to insult in vitro admininstration of $H_2O_2$ for two hours, after which PQQ is added in concentrations between 10 nM and less than 10 µM. In both studies, PQQ is found to be protective.

Example 4

Use of PQQ for Prevention/Reduction of Oxidative Stress In vivo

Rodent models of myocardial infarction are comparable to human systems. To demonstrate the ability of PQQ to salvage or protect myocardial damage, i.e., by determining the reduction or prevention of myocardial infarcts, a coronary artery ligation mouse model of myocardial infarction is used.

1. Rodent Model of Myocardial Infarction.

The coronary artery litigation model of myocardial infarction is used to investigate cardiac function in mice. The mouse is initially anesthetized with zylozine and ketamine, and after appropriate anesthesia is obtained, the trachea is intubated and positive pressure ventilation is initiated. The animal is placed supine with its extremities loosely taped and a median sternotomy is performed. The heart is gently exteriorized and a 6-O suture is firmly tied around the left anterior descending coronary artery. The heart is rapidly replaced in the chest and the thoracotomy incision is closed with 3-O purse string suture followed by skin closure with interrupted sutures or surgical clips. Animals are placed on a temperature regulated heating pad and closely observed during recovery. Supplemental oxygen and cardiopulmonary resuscitation are administered if necessary. After recovery, the mouse is returned to the animal care facility. Such coronary artery litigation in the mouse can produce large anterior wall myocardial infarctions. The 48 hour mortality for this procedure can be as high as 50, and there is variably in the size of the infarct produced by this procedure.

2. Based on range of effective PQQ concentrations obtained from the results of the ex vivo Langendorff experiments described PQQ is infused either via the tail vein or via the aorta in the mice prior to initiation of the infarct or after coronary artery litigation has been achieved. Control mice receive vehicle alone. Whether ∈PKC knockout mice and their wild-type littermates are studied depends on the results of the ex vivo experiments described in Example 2. After 48 hours the following measurements are carried out on the control and infracted mice:

a. Echocardiography. We have developed a method for obtaining 2-D and M-mode echocardiograms in unanesthetized mice. Left ventricular dimensions, function, wall thickness and wall motion can be reproducibly and reliably measured. These measurements are carried out in a blinded fashion to eliminate bias with respect to PQQ administration.

b. Hemodynamics. Hemodynamic measurements are used to determine the degree of left ventricular impairment. Mice are anesthesized with isoflorane. Through an incision along the right anterior neck the right carotid artery and the right jugular vein are isolated and cannulated with a pressure transducing catheter (Millar, SPR-612, 1.2 Fr). The following measurements are the made: heart rate, systolic and diastolic BP, mean arterial pressure, left ventricular systolic and end-diastolic pressure, and + and −dp/dt. Of particular utility are measurements of left ventricular end-diastolic pressure, progressive elevation of which correlated with the degree of myocardial damage.

c. Infarct size. Mice are then sacrificed for measurement of infarct size using standard TTC methodology.

These experiments test the hypothesis that systemic administration of PQQ either before or after coronary artery litigation leads to beneficial effects in intact animals, including the extent of hemodynamic abnormalities assessed by echocardiography and hemodynamic measurements, and reduction of infarct size. Initial measurements are proposed at 48 hours, but serial measurements can also be carried out in groups of mice over weeks-months, should it become appropriate to do so.

Limitations and Alternatives: In some mice, no infarction or only a small infarction may be produced; these mice can be identified by normal echocardiograms and normal hemodynamics (LV end-diastolic pressure <8 mm Hg). Such mice will not be sacrificed but can be used in the experiments described in Examples 1 and 2. If we find no difference between control and PQQ-treated mice, we will need to alter the dosing regimen, either using more drug or prolonging the infusion. We may also find that route of administration (intravenous vs. intra-aortic) will provide guidance as to dosing, i.e., we may find that direct aortic administration is superior to intravenous dosing, and will adjust the concentration of drug accordingly. We may also find that PQQ is more effective when given with another agent known to produce preconditioning, such as phenylephrine, a phorbol ester, sphingosine-1-phosphate, or the ganglioside GM-1.

Equivalents

Those skilled in the art will recognize, or be able to ascertain using no more than routine experimentation, numerous equivalents to the specific procedures described herein. Such equivalents are considered to be within the scope of the present invention and are covered by the following claims Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference.

What is claimed is:

1. A method of treating or reducing ischemia or reperfusion injury, the method comprising administering to a subject in need thereof an intravenous bolus of pyrroloquinoline quinone in an amount of 1 mg/kg, 2 mg/kg, 5 mg/kg or 10 mg/kg of the subject's body weight, wherein the administering step is performed after an ischemic insult and prior to, at, or after the onset of reperfusion, thereby treating or reducing the ischemia-reperfusion injury.

2. A method of treating or reducing ischemia or reperfusion iniury, the method comprising administering to a subiect in need thereof an intra-aortic bolus of pyrroloquinoline quinone in an amount of 1 mg/kg, 2 mg/kg, 5 mg/kg or 10 mg/kg of the subiect's body weight, wherein the administering step is performed after an ischemic insult and prior to, at, or after the onset of reperfusion, thereby treating or reducing the ischemia-reperfusion injury.

3. A method of reducing the severity of a cardiac injury caused by hypoxia or ischemia in a subject at risk of suffering said injury, the method comprising administering an intravenous bolus of pyrroloquinoline quinone in an amount of 1 mg/kg, 2 mg/kg, 5 mg/kg or 10 mg/kg of the subject's body weight, wherein the administering step is performed prior to a hypoxic or ischemic insult, thereby reducing the severity of the cardiac injury.

4. The method of claim 3, wherein the cardiac injury is selected from the group consisting of: myocardial infarction, cardiac arrest, heart surgery, heart transplantation, and traumatic cardiac injury.

5. The method of claim 4, wherein said traumatic cardiac injury is caused by aortic valve rupture.

6. A method of reducing the severity of a cardiac injury caused by hypoxia or ischemia in a subject at risk of suffering said injury, the method comprising administering an intra-aortic bolus of pyrroloquinoline quinone in an amount of 1 mg/kg, 2 mg/kg, 5 mg/kg or 10 mg/kg of the subject's body weight, wherein the administering step is performed prior to a hypoxic or ischemic insult, thereby reducing the severity of the cardiac injury.

7. The method of claim 4, wherein the size of the myocardial infarction is reduced.

* * * * *

UNITED STATES PATENT AND TRADEMARK OFFICE
CERTIFICATE OF CORRECTION

PATENT NO. : 7,276,514 B2 Page 1 of 1
APPLICATION NO. : 10/146566
DATED : October 2, 2007
INVENTOR(S) : Paul J. Davis It is certified that error appears in the above-identified patent and that said Letters Patent is hereby corrected as shown below:

Col. 20, lines 17-24;
Claim 2,

"2. A method of treating or reducing ischemia or reperfusion iniury, the method comprising administering to a subiect in need thereof an intra-aortic bolus of pyrrologuinoline quinone in an amount of 1 mg/kg, 2 mg/kg, 5 mg/kg or 10 mg/kg of the subiect's body weight, wherein the administering step is performed after an ischemic insult and prior to, at, or after the onset of reperfusion, thereby treating or reducing the ischemia-reperfusion injury."

should read:

--2. A method of treating or reducing ischemia or reperfusion injury, the method comprising administering to a subject in need thereof an intra-aortic bolus of pyrroloquinoline quinone in an amount of 1 mg/kg, 2 mg/kg, 5 mg/kg or 10 mg/kg of the subject's body weight, wherein the administering step is performed after an ischemic insult and prior to, at, or after the onset of reperfusion, thereby treating or reducing the ischemia-reperfusion injury.--

Signed and Sealed this

Eighteenth Day of December, 2007

JON W. DUDAS
*Director of the United States Patent and Trademark Office*